United States Patent
Cleary et al.

(10) Patent No.: US 8,095,223 B2
(45) Date of Patent: Jan. 10, 2012

(54) APPARATUS AND METHOD FOR INSERTING A CATHETER

(75) Inventors: Joseph Gordon Cleary, Bethlehem, PA (US); Telly Ousouljoglou, Bridgewater, NJ (US)

(73) Assignee: B. Braun Medical, Inc., Bethlehem, PA (US)

( * ) Notice: Subject to any disclaimer, the term of this patent is extended or adjusted under 35 U.S.C. 154(b) by 466 days.

(21) Appl. No.: 12/323,897

(22) Filed: Nov. 26, 2008

(65) Prior Publication Data

US 2010/0130923 A1    May 27, 2010

(51) Int. Cl.
*A61N 1/05* (2006.01)

(52) U.S. Cl. ...................................... 607/115
(58) Field of Classification Search ............. 606/41
See application file for complete search history.

(56) References Cited

U.S. PATENT DOCUMENTS

| | | | | |
|---|---|---|---|---|
| 3,561,445 A | * | 2/1971 | Katerndahl et al. | 604/159 |
| 4,637,404 A | * | 1/1987 | Gessman | 607/126 |
| 5,370,679 A | * | 12/1994 | Atlee, III | 607/124 |
| 6,086,008 A | * | 7/2000 | Gray et al. | 242/388.6 |
| 6,327,507 B1 | * | 12/2001 | Buchan | 607/115 |

FOREIGN PATENT DOCUMENTS

ES    1008463    4/1989

* cited by examiner

*Primary Examiner* — Carl H Layno
*Assistant Examiner* — Paula J Stice
(74) *Attorney, Agent, or Firm* — RatnerPrestia

(57) ABSTRACT

A delivery apparatus for a stimulating catheter has a conductive wire wound within a reel dispenser. The reel dispenser has a base portion and a rotating portion that are coupled at the axle with the rotating portion rotatable relative to the base portion. The proximal region of the conductive wire is in electrical connection with the axle of the dispenser. A method for delivering a stimulating catheter includes introducing the distal regions of the conductive wire and catheter into a subject, rotating the rotating portion of the reel dispenser relative to the base portion whereby the catheter and conductive wire are advanced into the subject, providing an electrical current to the conductive wire through the axle, and rewinding the rotating portion of the reel dispenser relative to the base portion whereby the conductive wire is retracted in a proximal direction through the catheter.

13 Claims, 6 Drawing Sheets

APPARATUS AND METHOD FOR INSERTING A CATHETER

BACKGROUND OF THE INVENTION

Catheters are used in a variety of medical applications. Typically, a catheter is transcutaneously introduced into an interior body lumen or cavity, such as a blood vessel or a hollow body organ. Depending on the type of medical procedure involved, there is often a need to position a catheter within the subject's body at a specific location, so that a targeted area can be treated. For example, some catheters are commonly used to deliver medicine or anesthetic fluid to a specific location within a subject.

"Stimulating catheters" have the ability to conduct electrical current and stimulate nerves in order to verify proper placement of the catheter. Stimulating catheters are commonly used to deliver anesthetic onto or near nerves in order to treat pain, or to identify specific nerves. In many types of catheters, a guidewire directs a catheter to the desired location in a subject and facilitates an accurate placement of the catheter. In the case of a stimulating catheter, the guidewire is electrically conductive, and is used to deliver an electrical current to a nerve. Typically, after the catheter is accurately positioned and an electrical current has been delivered, the guidewire is removed while the catheter stays in place. The catheter can then be used for further uses, such as for delivering anesthetic.

In addition to the difficulties associated with accurate catheter placement, handling and manipulation of catheters with internal guidewires can be very cumbersome. One particular difficulty with inserting and advancing catheters is the inability to maintain sufficient stiffness and control over both the guidewire and the catheter. For example, when a catheter is advanced, it becomes increasingly subject to kinking. Also, maintaining sufficient control over a guidewire is critical for avoiding the dangers of piercing the catheter or causing damage to a patient's system. To help lessen these problems, a dispensing device is typically used to insert a catheter and guidewire into a subject. For example, certain dispensers employ a rotating receptacle which aids in advancement of the catheter and guidewire. Unfortunately, conventional dispensers have a drawback in that typically they do not permit a user to maintain sufficient control throughout both the advancement and removal of the guidewire. For example, instead of enabling a user to reverse the guidewire in a controlled manner, they require additional steps, such as disassembling the dispenser in order to manually remove the guidewire. Furthermore, in the case of stimulating catheters, conventional dispensers typically do not permit the guidewire to maintain an electrical connection throughout both the advancement and removal of the guidewire. Accordingly, it is desirable to provide catheter dispensers which allow for safer handling and manipulation by enabling users to have increased control over the guidewire and catheter.

SUMMARY OF THE INVENTION

The present invention is directed to a delivery apparatus for a stimulating catheter and a method for delivery. A delivery apparatus according to the present invention comprises a reel dispenser with a conductive wire wound within the reel dispenser. The reel dispenser has a base portion and a rotating portion that are coupled at the axle. The rotating portion is rotatable relative to the base portion. The proximal region of the conductive wire is in electrical connection with the axle of the dispenser. In one embodiment, a catheter is disposed around at least a portion of the conductive wire, with the conductive wire in electrical communication with the catheter.

A method for delivery of a stimulating catheter according to the present invention includes introducing the distal regions of the conductive wire and catheter into a subject, rotating the rotating portion of the reel dispenser relative to the base portion whereby the catheter and conductive wire are advanced into the subject, providing an electrical current to the conductive wire through the axle, and rewinding the rotating portion of the reel dispenser relative to the base portion whereby the conductive wire is retracted in a proximal direction through the catheter.

According to another embodiment, a method for delivery includes detachably coupling the reel dispenser to an introducing needle, attaching a fluid supply source to the introducing needle, placing the distal regions of the catheter and conductive wire proximate a nerve in the subject, and administering an anesthetic through the catheter, whereby the anesthetic is delivered to the nerve.

It is to be understood that both the foregoing general description and the following detailed description are exemplary, but not restrictive, of the invention.

BRIEF DESCRIPTION OF THE DRAWINGS

The features of the invention believed to be novel and the elements characteristic of the invention are set forth with particularity in the appended claims. The figures are for illustration purposes only. The invention itself, however, may best be understood by reference to the detailed description which follows taken in conjunction with the accompanying figures in which:

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
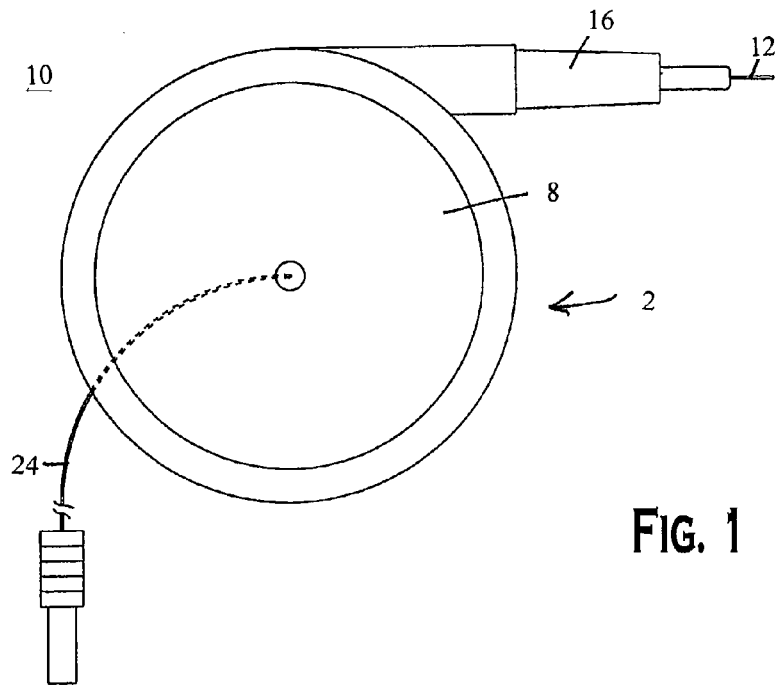
FIG. 1 illustrates a right side view of an embodiment of the present invention.
Figure 2:
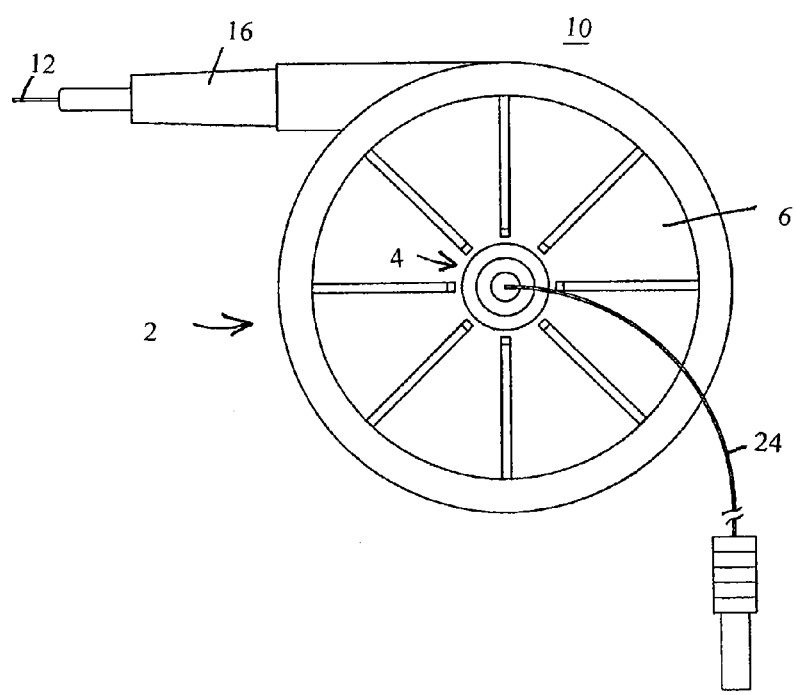
FIG. 2 illustrates a left side view of the embodiment of the present invention shown in FIG. 1.

Referring now to the figures, FIGS. 1 and 2 illustrate a delivery apparatus 10 for a stimulating catheter. As used herein, a "stimulating catheter" refers to any catheter, guidewire, or combination of catheter and guidewire that is electrically conductive. A reel dispenser 2 has an axle 4, a base portion 6 and a rotating portion 8 rotatable relative to the base portion 6. The base portion 6 and rotating portion 8 are coupled at the axle 4. Any known means for joining the rotating portion 8 and base portion 6 can be used, including any additional means that may be necessary for permitting the rotating portion 8 to be rotated while preventing a conductive wire 12 from becoming tangled or misaligned. According to one embodiment, the reel dispenser 2 has an outlet portion 16 to help direct the movement of a conductive wire 12 out of the reel dispenser 2 as the rotating portion 8 is rotated relative to the base portion 6. The reel dispenser 2 can be configured to have a variety of sizes, as needed. For example, reel dispensers of different sizes may be used to accommodate varying lengths of conductive wire and/or varying lengths of catheters. Any suitable material may be used for the features of the reel dispenser 2. Preferably, the features of the reel dispenser 2 are made of an impervious material, most preferably a plastic material.

Figure 6:
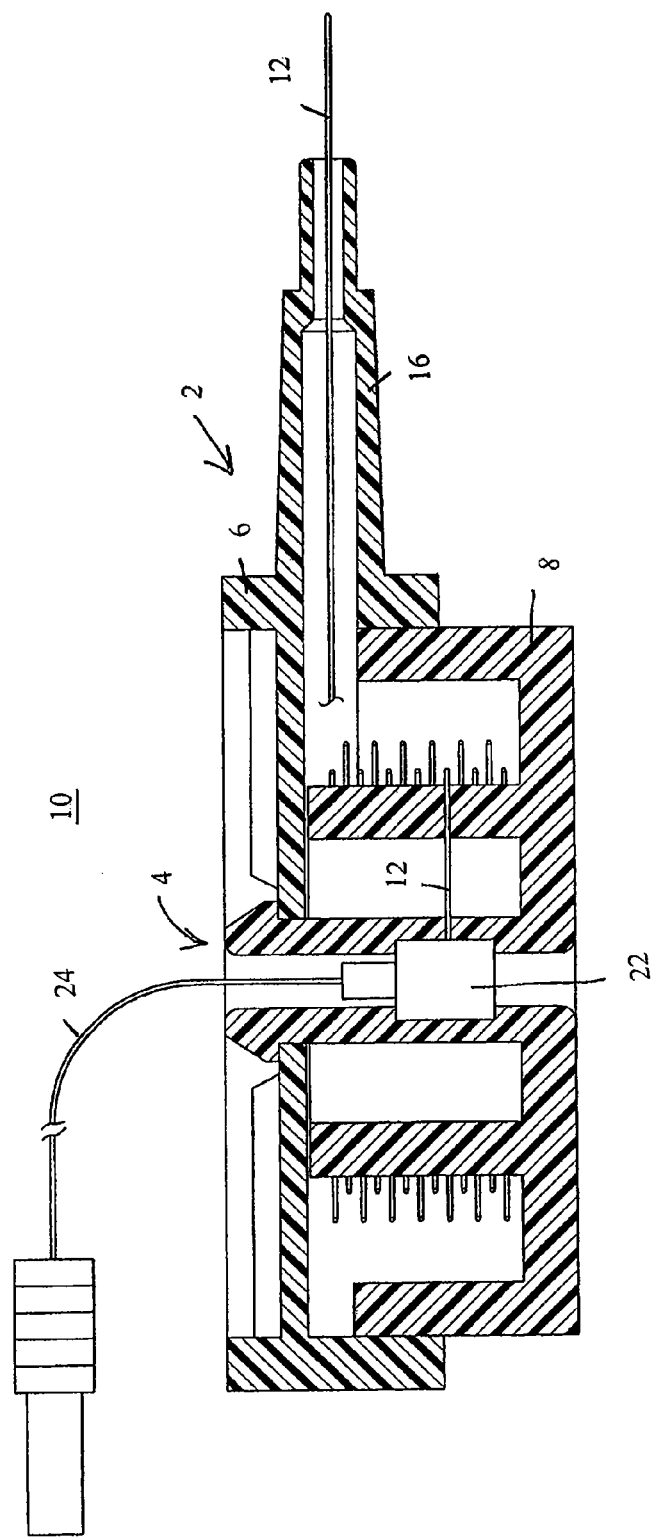
FIG. 6 illustrates a top cross-sectional view of the embodiment of the present invention shown in FIG. 1.

FIG. 6 illustrates a top cross-sectional view of an embodiment of the delivery apparatus 10. A conductive wire 12 is wound within the reel dispenser 2. The conductive wire 12 can be configured to have a variety of lengths, as needed. Thus, the number of times that the conductive wire 12 is wound around the axle 4 depends upon the size of the reel dispenser 2 (e.g., the circumference of the axle 4), and on the length of conductive wire 12 that is being used. The conductive wire 12 has a proximal region and a distal region, with the proximal region of the conductive wire 12 in electrical connection with the axle 4. As used herein, the term "proximal" is intended to mean a direction closer to a user of the delivery apparatus (e.g., a medical practitioner), and the term "distal" is intended to mean a direction farther from the user of the delivery apparatus.

According to one embodiment, the axle 4 is in electrical communication with an electrical stimulation source, which is capable of directly or indirectly providing an electrical current. For example, in one embodiment, the proximal region of the conductive wire 12 is in electrical connection with a terminal 22 that is located within the axle 4, and a second conductive wire 24 extends from the terminal 22 and plugs into an electrical stimulation source. A user can activate the electrical stimulation source to provide an electric current through the second conductive wire 24 to the terminal 22 in the axle 4, which, in turn, provides an electric current to the conductive wire 12. The conductive wire 12 is capable of maintaining electrical communication with the axle 4 and electrical stimulation source throughout the advancement and retraction of the conductive wire 12. Thus, the present invention enables a user to provide an electric current through the conductive wire 12 and to the subject at any time throughout the advancing and rewinding of the conductive wire 12.

Figure 3:
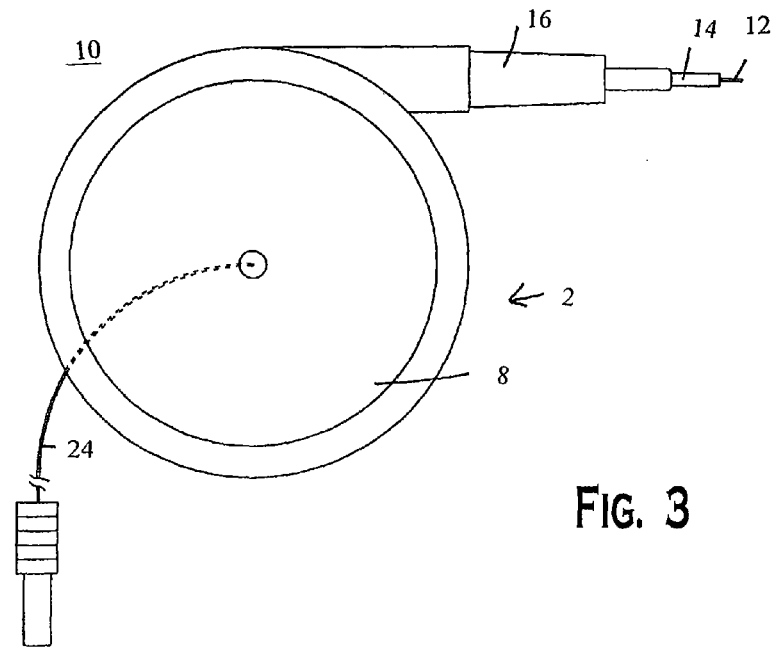
FIG. 3 illustrates a right side view of an embodiment of the present invention with a catheter.
Figure 4:
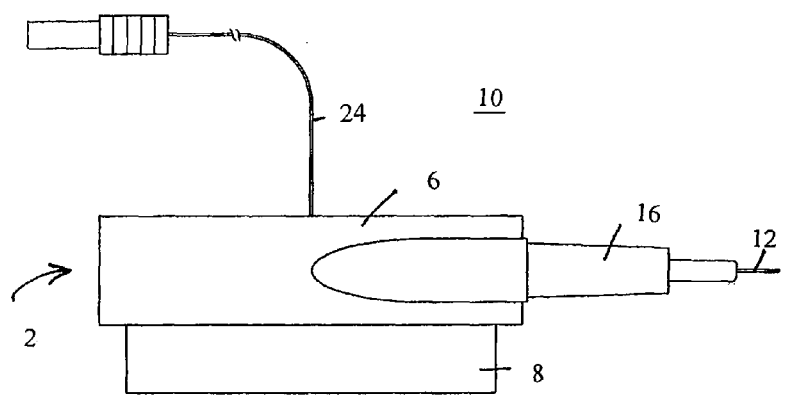
FIG. 4 illustrates a top plan view of the embodiment of the present invention shown in FIG. 1.
Figure 5:
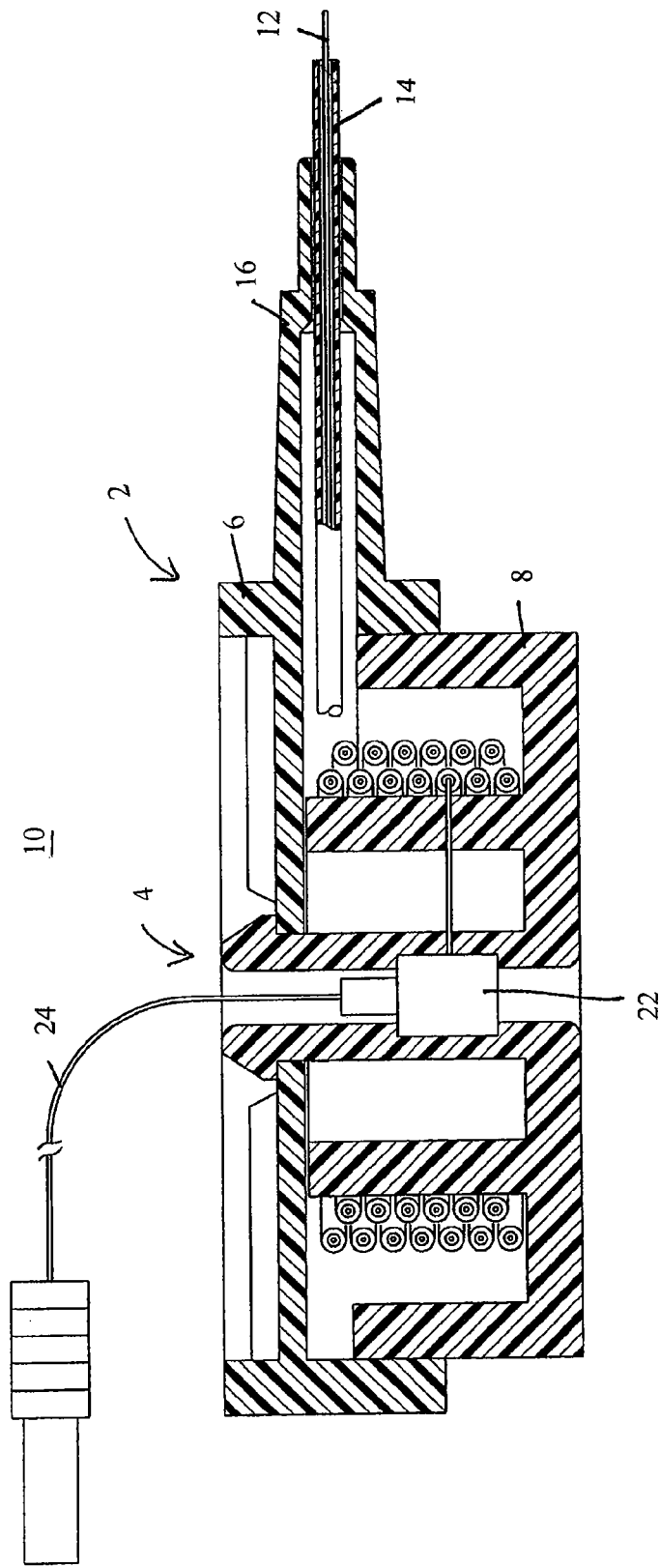
FIG. 5 illustrates a top cross-sectional view of the embodiment of the present invention shown in FIG. 3.

FIGS. 3 and 5 illustrate an embodiment of the present invention with a catheter 14 disposed around at least a portion of the conductive wire 12. The catheter 14 has a proximal region and a distal region. The catheter 14 is coiled around the axle 4 of the dispensing apparatus 10 with the conductive wire 12 moveably disposed within the catheter 14. Like the conductive wire 12, the catheter 14 can be configured to have a variety of lengths, as needed. Thus, the number of times that the catheter 14 is wound around the axle 4 depends upon the size of the reel dispenser 2 (e.g., the circumference of the axle 4), and on the length of catheter 14 that is being used. In a preferred embodiment, at least a portion of the catheter 14 is electrically conductive (e.g., an internal conductive wire disposed within the catheter and at the tip of the catheter). The conductive wire 12 is in electrical communication with the catheter 14, and the catheter 14 is capable of conveying an electrical impulse to a desired location in a subject. In one embodiment, the conductive wire 12 has an insulated portion and an exposed portion, with the exposed portion capable of conveying an electrical impulse to the catheter 14.

Figure 7:
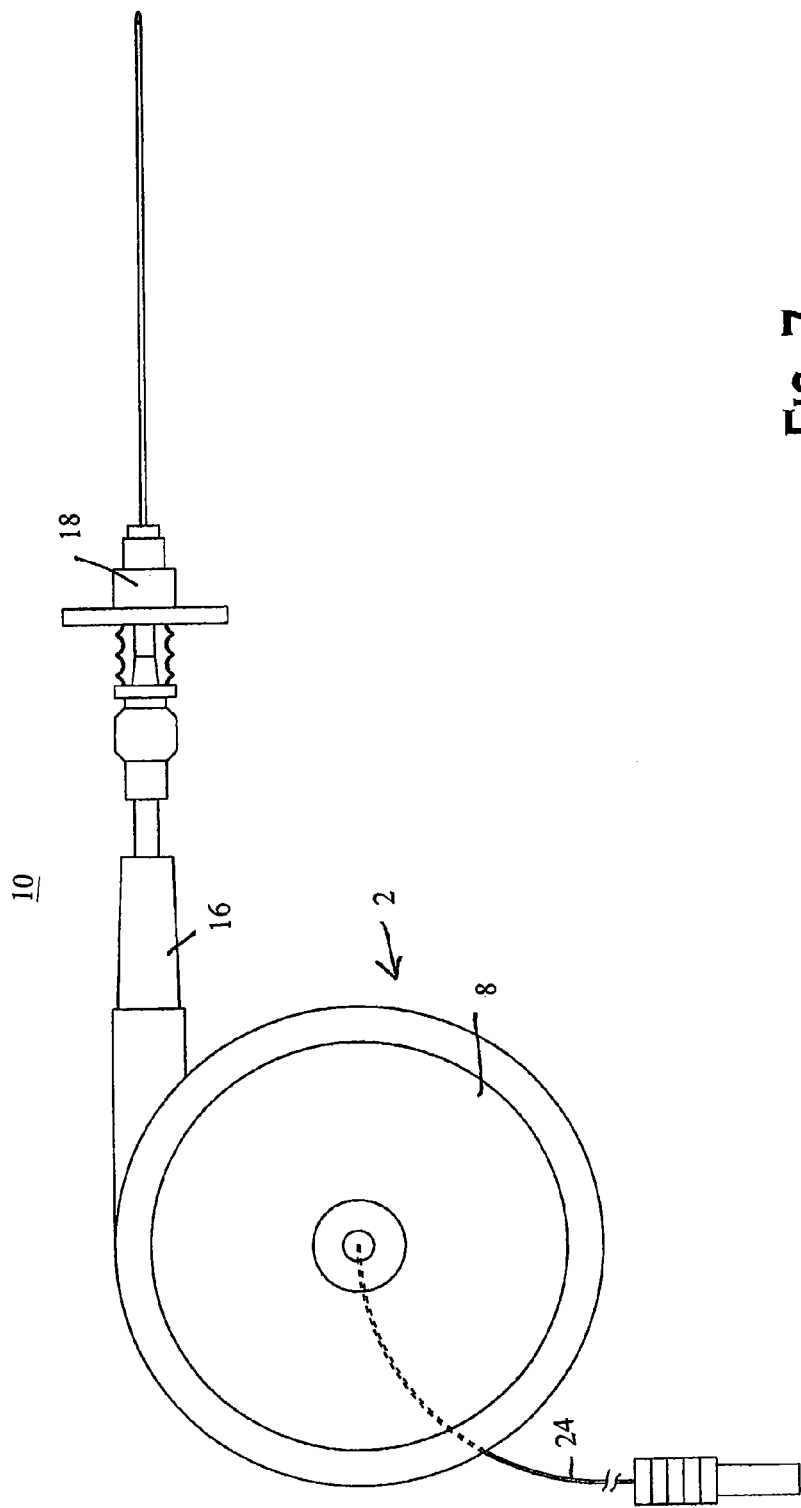
FIG. 7 illustrates a right side view of an embodiment of the present invention with an introducing device.

FIG. 7 illustrates an embodiment of the present invention with an introducing device 18. An introducing device 18, such as an introducing needle, assists a user in introducing the conductive wire 12 and/or catheter 14 into a subject. The introducing device 18 is detachably coupled to the reel dispenser 2, preferably to the outlet 16 of the reel dispenser 2. A fluid supply source may be attached to the introducing device so that fluids, such as anesthetic, can be administered to a subject.

A method for delivery of a stimulating catheter according to an embodiment of the present invention comprises introducing the distal regions of the conductive wire 12 and catheter 14 into a subject. The rotating portion 8 of the reel dispenser 2 is rotated relative to the base portion 6, whereby the catheter 14 and conductive wire 12 are advanced into the subject. To rotate the rotating portion 8, a user preferably grasps the base portion 6 in one hand while rotating the rotating portion 8 with the other hand. By rotating the rotating portion 8, the conductive wire 12 and catheter 14, which are wound around the axle 4 of the reel dispenser 2, advance around the axle 4, out of the reel dispenser 2, and into a subject.

The conductive wire 12 inside the catheter 14 permits even forwarding of the catheter 14 and reduces the chance of binding or kinking of the catheter 14. The distal regions of the catheter 14 and conductive wire 12 can be accurately placed in a desired location in the subject, such as proximate a nerve or directly on a nerve, and an electrical current is provided to the conductive wire 12 through the axle 4. The conductive wire 12 is capable of conveying the electrical current to the catheter 14, which conveys an electrical current to a specific location in the subject's body, such as a nerve. Alternatively, the conductive wire 12 directly conveys an electrical current to a desired location in the subject.

In a preferred embodiment, a user detachably couples the outlet portion 16 of the reel dispenser 2 to an introducing device 18, and inserts a distal portion of the introducing device 18 into a subject. A fluid supply source may be attached to the introducing device 18 for administering fluids, such as a medicine or anesthetic, through the catheter 14 to a desired location in the subject, such as a nerve. The administration of a medicine or anesthetic preferably occurs after an electrical current has been conveyed to a desired location in the subject, and after the conductive wire 12 has been removed from the subject.

The conductive wire 12 is preferably removed from the subject by rewinding the rotating portion 8 of the reel dispenser 2 relative to the base portion 6, whereby the conductive wire 12 is retracted in a proximal direction through the catheter 14. Because the reel dispenser 2 permits rewinding of the conductive wire 12, it is not necessary for the user to disassemble the reel dispenser 2 in order to remove the conductive wire 12. This enables the user to maintain control of the conductive wire 12 throughout both advancement and retraction, and reduces the risk of the conductive wire 12 piercing the subject or inflicting other trauma while being retracted from the subject. Any known means for rewinding the conductive wire 12 into the reel dispenser 2 can be used. For example, the rewinding step may comprise rotating the rotating portion 8 in a direction that is opposite the first direction in which the conductive wire 12 was advanced into the subject. The conductive wire 12 can also be retracted in a proximal direction through the catheter 14 by pulling the reel dispenser 2 in a proximal direction. Preferably, the rewinding step occurs following the electrical stimulation of a desired location in the subject.

Figure 8:
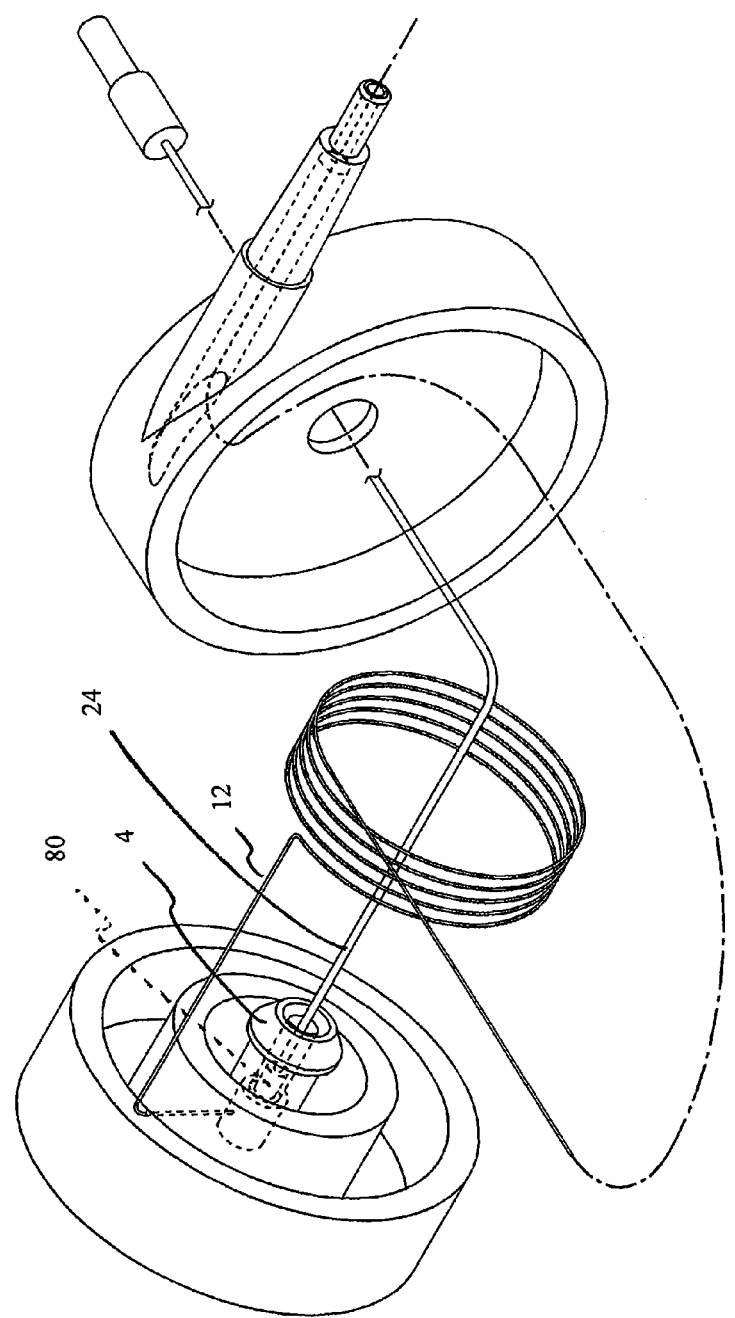
FIG. 8 illustrates an exploded view of the embodiment of the present invention shown in FIG. 1.

The conductive wire 12 is capable of maintaining electrical communication with the axle 4 throughout the introducing, advancing, and rewinding of the conductive wire. The axle 4, in turn, is capable of maintaining electrical communication with an electrical stimulation source throughout the introducing, advancing, and rewinding of the conductive wire 12. Thus, as discussed above, a user is capable of conveying an electrical impulse to the subject or to the conductive catheter at any time, including during the steps of introducing, advancing, and rewinding the conductive wire 12. FIG. 8 illustrates one embodiment where wire 12 is electrically mated with plug 80 housed within axle 4. Conductive wire 24 is thus free to spin within axle 4 and not be twisted during operation of the device.

Although preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A delivery apparatus for an electrically stimulating catheter comprising:
   a reel dispenser having an axle, a base portion and a rotating portion rotatable relative to the base portion, the base portion and rotating portion coupled at the axle;
   a catheter disposed within the reel dispenser, the catheter coiled around the axle and having a proximal region and a distal region;
   a plug housed within the axle;
   a first conductive wire moveably disposed within the catheter, the first conductive wire having a proximal region and a distal region, the proximal region of the first conductive wire in electrical connection with the plug; and
   a second conductive wire having a proximal region and a distal region, the proximal region of the second conductive wire plugged into an electrical stimulation source and the distal region of the second conductive wire extending through the axle in electrical communication with the plug, the second conductive wire free to rotate inside the axle as the rotating portion is rotated relative to the base portion.

2. The apparatus of claim 1, wherein the catheter is capable of conveying an electrical impulse to a desired location in a subject.

3. The apparatus of claim 1, wherein the reel dispenser further comprises an outlet portion to direct the movement of the wire as the rotating portion is rotated relative to the base portion.

4. The apparatus of claim 1, wherein the first conductive wire comprises an insulated portion and an exposed portion.

5. The apparatus of claim 1 further comprising an introducing needle detachably coupled to the reel dispenser.

6. A method for delivery of an electrically stimulating catheter into a subject, comprising the steps of:
   providing a reel dispenser having:
      an axle, a base portion and a rotating portion rotatable relative to the base portion, the base portion and rotating portion coupled at the axle;
      a catheter disposed within the reel dispenser, the catheter coiled around the axle and having a proximal region and a distal region,
      a plug housed within the axle;
      a first conductive wire moveably disposed within the catheter and coiled around the axle, the first conductive wire having a proximal region and a distal region, the proximal region of the first conductive wire in electrical connection with the plug; and
      a second conductive wire having a proximal region and a distal region, the proximal region of the second conductive wire plugged into an electrical stimulation source and the distal region of the second conductive wire extending through the axle in electrical communication with the plug, the second conductive wire free to rotate inside the axle as the rotating portion is rotated relative to the base portion;
   introducing the distal regions of the first conductive wire and catheter into a subject;
   rotating the rotating portion of the reel dispenser relative to the base portion, wherein the catheter and first conductive wire are advanced into the subject;
   providing an electrical current through the second conductive wire and axle to the first conductive wire; and
   rewinding the rotating portion of the reel dispenser relative to the base portion, wherein the first conductive wire is retracted in a proximal direction through the catheter.

7. The method of claim 6 further comprising the step of detachably coupling the reel dispenser to an introducing needle prior to the introducing step.

8. The method according to claim 7 further comprising the step of attaching a fluid supply source to the introducing needle.

9. The method of claim 6 further comprising the step of placing the distal regions of the catheter and first conductive wire proximate a nerve in the subject.

10. The method of claim 9 further comprising the step of administering an anesthetic through the catheter, wherein the anesthetic is delivered to the nerve.

11. A delivery apparatus for an electrically stimulating catheter comprising:
    a reel dispenser having an axle, a base portion and a rotating portion rotatable relative to the base portion, the base portion and rotating portion coupled at the axle;
    a catheter disposed within the reel dispenser, the catheter coiled around the axle and capable of conveying an electrical impulse to a subject;
    a plug housed within the axle;
    a first conductive wire moveably disposed within the catheter and coiled around the axle, the first conductive wire having a proximal region and a distal region, the proximal region in electrical connection with the plug and the distal region in electrical communication with the catheter; and
    a second conductive wire having a proximal region and a distal region, the proximal region of the second conductive wire plugged into an electrical stimulation source and the distal region of the second conductive wire extending through the axle in electrical communication with the plug, the second conductive wire free to rotate inside the axle as the rotating portion is rotated relative to the base portion.

12. A method for delivery of an electrically stimulating catheter into a subject, comprising the steps of:
    providing a reel dispenser having an axle, a base portion and a rotating portion rotatable relative to the base portion, the base portion and rotating portion coupled at the axle, a catheter disposed within the reel dispenser, a plug housed within the axle, the catheter coiled around the axle and having a proximal region and a distal region, a first conductive wire moveably disposed within the catheter and coiled around the axle, the first conductive wire having a proximal region and a distal region, the proximal region of the first conductive wire in electrical connection with the plug, and a second conductive wire having a proximal region and a distal region, the proximal region of the second conductive wire plugged into an electrical stimulation source and the distal region of the second conductive wire extending through the axle in electrical communication with the plug, the second conductive wire free to rotate inside the axle as the rotating portion is rotated relative to the base portion;

providing an electrical current through the second conductive wire and axle to the first conductive wire;

introducing the distal regions of the first conductive wire and catheter into a subject;

rotating the rotating portion of the reel dispenser relative to the base portion in a first direction, wherein the catheter and first conductive wire are advanced into the subject; and rotating the rotating portion of the reel dispenser relative to the base portion in a direction opposite the first direction, wherein the first conductive wire is retracted in a proximal direction through the catheter.

13. A method for delivery of an electrically stimulating catheter into a subject, comprising the steps of:

providing a reel dispenser having:

an axle, a base portion and a rotating portion rotatable relative to the base portion, the base portion and rotating portion coupled at the axle;

a catheter disposed within the reel dispenser, the catheter coiled around the axle and having a proximal region and a distal region;

a plug housed within the axle;

a first conductive wire moveably disposed within the catheter and coiled around the axle, the first conductive wire having a proximal region and a distal region, the proximal region of the first conductive wire in electrical connection with the plug; and a second conductive wire having a proximal region and a distal region, the proximal region of the second conductive wire plugged into an electrical stimulation source and the distal region of the second conductive wire extending through the axle in electrical communication with the plug, the second conductive wire free to rotate inside the axle as the rotating portion is rotated relative to the base portion;

introducing the distal regions of the first conductive wire and catheter into a subject;

rotating the rotating portion of the reel dispenser relative to the base portion, wherein the catheter and first conductive wire are advanced into the subject;

providing an electrical current through the second conductive wire and axle to the first conductive wire; and pulling the reel dispenser in a proximal direction, wherein the first conductive wire is retracted in a proximal direction through the catheter.

* * * * *